United States Patent [19]

Kulka

[11] 4,168,248

[45] Sep. 18, 1979

[54] PERFUME COMPOSITIONS

[75] Inventor: Kurt Kulka, New York, N.Y.

[73] Assignee: Fritzsche Dodge & Olcott Inc., New York, N.Y.

[21] Appl. No.: 880,580

[22] Filed: Feb. 23, 1978

Related U.S. Application Data

[63] Continuation-in-part of Ser. No. 305,793, Nov. 13, 1972, abandoned, Ser. No. 42,495, Jun. 1, 1970, abandoned, Ser. No. 750,459, Aug. 6, 1968, abandoned, and Ser. No. 559,708, Jun. 23, 1966, abandoned.

[51] Int. Cl.[2] .......................... A61K 7/46; C11B 9/00

[52] U.S. Cl. ...................................... 252/522; 424/65

[58] Field of Search .......................................... 252/522

[56] References Cited

U.S. PATENT DOCUMENTS

| | | | |
|---|---|---|---|
| 2,833,811 | 5/1958 | Surmatis | 252/522 |
| 2,918,412 | 12/1959 | Wood | 252/522 |

OTHER PUBLICATIONS

Cason, Journ. of Org. Chem., 1948, vol. 13, pp. 227-238.

Cason, Chem. Abs., 1948, vol. 42, pp. 4925-4926.

*Primary Examiner*—Dale R. Ore

*Attorney, Agent, or Firm*—Frank M. Nolan

[57] ABSTRACT

The perfume compositions of this invention include one or more of 3-methylnonan-3-ol, 3-methyl-1-nonen-3-ol, 3-methylnonan-1-ol, 3-methyl-2-nonen-1-ol and the monocarboxylic acid esters of these alcohols. The perfume compositions also contain a perfume component, the odoriferous properties of which are enhanced and modified by said alcohols or esters of the alcohols without chemical reaction.

15 Claims, No Drawings

PERFUME COMPOSITIONS

This application is a continuation-in-part application of the applications Ser. No. 305,793, filed Nov. 13, 1972, now abandoned, Ser. No. 42,495, filed June 1, 1970, now abandoned, Ser. No. 750,459, filed Aug. 6, 1968, now abandoned, and Ser. No. 559,708, filed June 23, 1966, now abandoned.

This invention relates to perfume compositions containing 3-methylnonan-3-ol, 3-methyl-1-nonen-3-ol, 3-methylnonan-1-ol, 3-methyl-2-nonen-1-ol and monocarboxylic acid esters of such alcohols.

Certain olfactory substances cannot be used as components in some perfume compositions because of their reactivity with other perfume components. For example, components such as acetylenic derivatives have significantly high reactivity which restricts their use in perfume compositions.

In accordance with one aspect of this invention, wide variations in perfume odors may be achieved in perfume compositions by including in the formulation one or more of 3-methylnonan-3-ol, 3-methyl-1-nonen-3-ol, 3-methylnonan-1-ol, 3-methyl-2-nonen-1-ol or monocarboxylic acid esters of these alcohols. The perfume compositions of this invention comprise, in addition to at least 1% of said alcohols or esters, at least 9% by weight of one or a plurality of perfume components, the odoriferous properties of which are enhanced or modified, wihout chemical reaction, by the specified alcohols or certain of their monocarboxylic acid esters.

The 3-methylnonan-1-ol, 3-methyl-2-nonen-1-ol and the monocarboxylic acid esters of all of the specified alcohols of the invention are new compounds.

The monocarboxylic acid esters of the specified alcohols are produced by reaction of the specified alcohol with one of the following monocarboxylic acids: saturated 1 to 7 carbon atoms aliphatic monocarboxylic acids, unsaturated 3 to 7 carbon atoms aliphatic monocarboxylic acids having one double bond, cyclopentane carboxylic acid, cyclohexane carboxylic acid, salicylic acid, cinnamic acid, hexahydrobenzoic acid or p-toluic acid.

Examples of saturated aliphatic monocarboxylic acids are acetic, propionic, butyric, pentanoic, hexanoic and heptanoic acids.

Examples of unsaturated aliphatic monocarboxylic acids having one double bond are acrylic, crotonic, tiglic acids; a pentenoic, hexenoic or heptenoic acid.

The 3-methylnonan-3-ol, 3-methyl-1-nonen-3-ol, 3-methylnonan-1-ol, 3-methyl-2-nonen-1-ol, or the monocarboxylic acid ester of any of the foregoing alcohols is thoroughly mixed with at least 9% by weight of the perfume component or components. Desirably, the specified alcohol or specified ester comprises 1 to 91% by weight, preferably 2 to 88% by weight, and more advantageously 5 to 85% by weight of the perfume composition.

The monocarboxylic acid esters of 3-methylnonan-3-ol or 3-methyl-1-nonen-3-ol may be produced by mixing the required alcohol and the anhydride of the required monocarboxylic acid with a suitable solvent, such as toluene. The formed acid is removed as an azeotrope with the solvent by distillation through a column such as a 14" Vigreux column. Any excess anhydride and the solvent are removed by distillation under vacuum at steam bath temperature. A solvent, such as benzene, is added to the crude reaction product, and the mixture is neutralized to remove any remaining acid or acid anhydride. The mixture is then subjected to fractional distillation through a column such as a 14" Vigreux column to obtain the desired ester.

Alternatively, an acid halide of the required carboxylic acid, such as the acid chloride, may be employed. In such case, the required alcohol is mixed with a tertiary base, such as pyridine, and preferably a solvent, such as toluene or benzene.

To this solution is gradually added, with agitation, the required acid chloride. The reaction mixture is then heated to 50°-60° C. to complete the reaction. The formed tertiary base hydrochloride is removed by washing with water and the crude desired ester is rectified by fractionation in vacuum.

The 3-methylnonan-3-ol and the 3-methyl-1-nonen-3-ol utilized as components in the perfume compositions of this invention and for the production of the monocarboxylic acid esters also employed as components of the compositions of this invention, are known compounds. A convenient starting material for both of these alcohols is the acetylenic alcohol 3-methyl-1-nonyne-3-ol. This acetylenic alcohol may be prepared according to the procedures described in U.S. Pat. No. 2,385,547, granted on Sept. 25, 1945 on an application of Everett S. Smith, or U.S. Pat. No. 3,082,260 granted on Mar. 19, 1963 on an application of Robert J. Tedeschi et al. The 3-methylnonan-3-ol is produced by the hydrogenation of 3-methyl-1-nonyne-3-ol in accordance with the procedure described in U.S. Pat. No. 2,908,722 granted on Oct. 13, 1959 on an application of John Alvin Casey. The 3-methyl-1-nonen-3-ol may be prepared by partial hydrogenation of 3-methyl-1-nonyn-3-ol.

The 3-methyl-2-nonen-1-ol employed in the perfume compositions of this invention and as a reactant in the production of monocarboxylic acid esters of that alcohol is produced by employing 3-methyl-1-nonen-3-ol as the starting material. The starting alcohol is reacted in the absence of solvents with a monocarboxylic acid such as acetic acid together with sulfuric acid and maintained at a temperature of about 50° to 80° C. The progress of the reaction is followed by I.R. spectroscopy. Under these conditions there is dehydration of the tertiary alcohol, 3-methyl-1-nonen-3-ol to a hydrocarbon, allylic rearrangement of the tertiary alcohol to the primary alcohol, 3-methyl-2-nonen-1-ol and partial esterification with formation of a monocarboxylic acid ester of 3-methyl-2-nonen-1-ol. A solution of an alkali metal hydroxide, such as sodium hydroxide and a suitable solvent such as methanol is added to the reaction product and the solution refluxed for three to six hours to saponify the esters. The solvent is removed by distillation under a slight vacuum. The remaining reaction product is then washed successively with water, an alkali metal bicarbonate solution and water. Fractional distillation under vacuum is conducted to obtain a fraction containing the 3-methyl-2-nonen-1-ol. The fraction distilling at 10 mm and a temperature of 110°-111° C. is recovered and contains primarily the 3-methyl-2-nonen-1-ol. The corresponding saturated alcohol, 3-methylnonan-1-ol is produced by hydrogenation of the unsaturated alcohol 3-methyl-2-nonen-1-ol in the presence of Raney nickel or other suitable catalyst.

The specified alcohols or their esters enhance the olfactory properties of the perfume component or components of the perfume compositions, giving a more aesthetic physical impact. This result does not stem from a chemical reaction which would change the chemical structure of the perfume components. The effect of the specified alcohols or their esters on the perfume components is olfactory. The wide variation of this enhancing value of the specified alcohols or their esters on the odoriferous properties of the perfume components of perfume compositions is illustrated by the later described Examples XXIII through XXX.

The specific examples teach the perfumer the identity of the specified alcohols and esters and the technique of varying and modifying the olfactory properties of perfume components to achieve a wide range of perfume compositions. Although similar or even identical perfume components are found in the specific examples, the marked difference in the odoriferous properties of the perfume compositions as effected by the specified alcohols or their esters is most evident. A whole range of perfume compositions-rose, levendar, gardenia, jasmine, lilac, for example—result from varying the types and amounts of the specified alcohols or esters employed.

A more comprehensive understanding of this invention is obtained by reference to the following examples:

EXAMPLE I

PREPARATION OF 3-METHYLNONAN-3-YL-ACETATE

40 G. (0.25 mole) of 3-methylnonan-3-ol, 60 g. of acetic anhydride and 250 ml. of toluene were mixed and the formed acetic acid removed as an azeotrope with toluene by distillation through a 14" Vigreux column. This procedure required about 12 hours. The temperature in the flask was 118°-125° C. and the temperature of vapor was 106°-112° C. during the distillation. The excess acetic anhydride and toluene were removed by distillation under vacuum at steam bath temperature. To the crude remaining reaction product was added 75 ml. of benzene, and the solution was washed successively with 75 ml. of water, 75 ml. of sodium carbonate solution, 75 ml. of sodium bicarbonate solution and 75 ml. of water. The solvent was removed by distillation and the product was fractionated through a 14" Vigreux column. The following fractions were obtained:

| | Temp. Vapor | Temp. Flask | Vac. | cc. | wt. | R.I. 20° |
|---|---|---|---|---|---|---|
| First Fraction | 96°-97° | 99°-100° | 10 | 4 | 3.1 | 1.4283 |
| Second Fraction | 97° | 100°-100° | 10 | 48 | 45. | 1.4270 |
| Third Fraction | | Flashed: | | 5 | 3.2 | 1.4271 |
| | | Residue: | | | -.5 | |
| | | Total: | | | 50.8 | |

The second fraction represents the desired ester. An infrared examination confirmed that the desired ester was obtained. Wet analysis proved this ester to be of 99% purity.

The 3-methylnonan-3-ol used in this and other examples for the production of carboxylic acid esters of that alcohol was prepared by hydrogenating 3-methyl-1-nonyne-3-ol under the following conditions:

| | |
|---|---|
| Initial pressure | 50 lbs. |
| Solvent | none. |
| Catalyst | Raney-Nickel. |
| Time of hydrogenation | approximately ½ hour. |
| Reaction-temperature | very exothermic - no cooling was applied. |

-continued

| | |
|---|---|
| Reacted | 100. g (of the acetylenic alcohol). |

After completion of the reaction, the product was liberated from the catalyst by filtration and fractionated through a 14" Vigreux column.

| Fraction | Temp. Vapor | Temp. Flask | Vac. | cc. | wt. | R.I. 20° |
|---|---|---|---|---|---|---|
| I. | 83°-97° | 97-99 | 15 | 7 | 6.5 | 1.4291 |
| II. | 97° | 99-121 | 15 | 104 | 83.5 | 1.4367 |
| | flashed: | | | 4 | 3.4 | 1.4367 |
| | | Residue: | | | 1. | |
| | | Total: | | | 94.4 g. | |

Fraction No. II was 99.5% by VPC.

EXAMPLE II

PREPARATION OF 3-METHYLNONAN-3-YL-ISOBUTYRATE

40 G. (0.25 mole) of 3-methylnonan-3-ol, 80 g. of isobutyric anhydride and 600 ml. of xylene were mixed and the formed isobutyric acid was removed as an azeotrope with xylene by distillation through a 14" Vigreux column. The procedure required about 9 hours. The temperature of the vapor was 116°-139° C. and the temperature of the flask was 147°-160° C. during the distillation. The excess isobutyric anhydride and solvent were removed fom the reaction product by distillation at steam bath temperature under ejector vacuum through a 14" Vigreux column. To the remaining crude reaction product was added 75 ml. of benzene and the resulting solution was washed successively with 100 ml. of water, 100 ml. of sodium carbonate solution, 100 ml. of sodium bicarbonate solution and 100 ml. of water. The reaction product was fractionated through a 14" Vigreux column. The following fractions were obtained:

| | Temp. Vapor | Temp. Flask | Vac. | cc. | wt. | R.I. 20° |
|---|---|---|---|---|---|---|
| First Fraction | 101° | 104°-105° | 5 | 4 | 2.8 | 1.4275 |
| Second Fraction | 101° | 105°-109° | 5 | 55 | 50. | 1.4290 |
| Third Fraction | | Flashed: | | 4 | 3. | 1.4290 |
| | | Residue: | | | 0.9 | |
| | | Total: | | | 56.7 g. | |

The second fraction represented the desired ester. As infrared examination confirmed that the desired ester was obtained. Wet analysis proved this ester to be of 99% purity.

EXAMPLE III

PREPARATION OF 3-METHYLNONAN-3-YL-BENZOATE 40.0 G. (0.25 mole) of 3-methylnonan-3-ol, 20. g. of pyridine and 60 ml. of toluene are combined and cooled to 5° C. under agitation. To the resulting solutin is added, under agitation, over a period of 1 to 2 hours while maintaining the reaction temperature between 5°-15° C., a solution of 35.15 g. (0.25 mole) of benzoyl chloride, dissolved in 30 ml. of toluene. The source of cooling is removed and the reaction mixture is agitated overnight, permitting the temperature of the reaction mixture to rise to room temperature (25°-30° C.). After completion of the reaction, the formed pyridine hydrochloride is removed by successive washings with 100 ml. of warm water. The solvent is removed by distillation and the desired ester is rectified by fractional distillation in a vacuum, preferably at 1 mm.

EXAMPLE IV

PREPARATION OF 3-METHYLNONEN-3-YL-ACETATE

156 G. (1 mole) of 3-methyl-1-nonen-3-ol, 112.2 g. (1.1 mole) of acetic anhydride and 150 g. of m-xylene are mixed in a reaction flask and heated. The formed acetic acid is removed by distillation as an azeotrope consisting of 72.5% by weight of acetic acid and 27.5% by weight of m-xylene, boiling at 115.4° C. at 760 mm. pressure through a 1¼ ft. Vigreux column.

After the theoretical amount of acetic acid is removed, the reaction mixture is cooled and washed successively with 150 ml. of warm water, 150 ml. of aqueous sodium carbonate solution, 150 ml. of sodium bicarbonate solution and twice with 100 ml. of warm water. Through this washing procedure, the unreacted acetic anhydride is first hydrolyzed to acetic acid and consequently removed from the reaction mixture. The reaction mixture is then freed from the solvent by distillation under vacuum and the desired ester is rectified by fractional distillation in a vacuum, preferably at 1 mm.

The 3-methyl-1-nonen-3-ol used in this and other examples for the production of carboxylic acid esters of that alcohol was a commercially obtained product.

EXAMPLE V

PREPARATION OF 3-METHYL-1-NONEN-3-YL-ISOBUTYRATE

156 G. (1 mole) of 3-methyl-1-nonen-3-ol, 174 g. (1.1 moles) of isobutyric anhydride and 700 ml. of m-xylene are mixed in a reaction flask and heated. The formed isobutyric acid is removed as an azeotrope consisting of 14% by weight of isobutyric acid and 85% by weight of m-xylene boiling at 136.8° C. at 760 mm. pressure, through a 1¼" Vigreux column. After approximately 500 ml. of the azeotrope has been removed, another 700 ml. of m-xylene is added to the reaction flask and the process is continued. After the theoretical amount of isobutyric acid has been removed, the reaction mixture is cooled and is washed successively with 150 ml. of warm water, 150 ml. of aqueous sodium carbonate solution, 150 ml. of aqueous sodium bicarbonate solution and twice with 100 ml. of warm water. By this washing procedure, the unreacted isobutyric anhydride is first hydrolyzed to isobutyric acid and is then consequently removed from the reaction mixture. The reaction is then freed from the solvent by distillation under vacuum and the desired ester is rectified by fractional distillation in a vacuum, preferably at 1 mm.

If an unsaturaed aliphatic carboxylic acid ester, such as 3-methylnonan-3-yl-tiglate, 3-methyl-1-nonen-yl-acrylate or 3-methylnonan-3-yl-crotonate is used in this invention, the procedural steps of Example V may be followed for the production of such esters.

EXAMPLE VI

PREPARATION OF 3-METHYL-NONEN-3-YL-FORMATE

156 G. (1 mole) of 3-methyl-1-nonen-3-ol, 96.8 g. (1.1 moles) of formic-acetic anhydride are mixed and cooled in an ice-water bath to approximately 5° C. Under agitation and continuous cooling, 5 g. of phosphoric acid (commercial grade, approximately 88% purity) is added. The reaction mixture is kept at 5°-8° C. with cooling for 8 hours and the temperature is then permitted to rise gradually to room temperature (25°-30° C.). The progress of the reaction is followed by taking samples at convenient intervals and by examination of their infrared spectra. After completion of the reaction, the reaction mixture is poured on 200 g. of ice and is taken up with 300 ml. of benzene or another suitable solvent such as hexane, heptane or toluene. The organic phase (solvent plus reaction product) is separated from the water phase. It is washed with a dilute cold aqueous sodium bicarbonate solution (approximately 2×250 ml. of 2% aqueous sodium bicarbonate solution) and eventually, with 150 ml. of cold water, twice. The solvent is then removed from the reaction mixture by distillation under vacuum and the desired ester is rectified by fractional distillation in a vacuum, preferably at 1 mm.

The mixed anhydride, acetic-formic anhydride, is prepared according to the procedure of A. Behal, described in *Ann.chim. phys.,* 20, 417 (1900).

EXAMPLE VII

PREPARATION OF 3-METHYL-2-NONEN-1-OL

To a solution of 550 ml. of water, 50 g. of sulfuric acid (conc. 86%) and 100 mg. of acetic acid was added 500 g. of 3-methyl-1-nonen-3-ol. The reaction mass was agitated and kept at a temperature of 66° C. The progress of the reaction was followed by I.R. spectroscopy. It was established that under the conditions involved in this process, the following reactions took place simultaneously:

1. Dehydration of the tertiary alcohol (3-methyl-1-nonen-3-ol) to a hydrocarbon.
2. Allylic rearrangement of the tertiary alcohol to the primary alcohol, i.e. 3-methyl-2-nonen-1-ol.
3. Partial esterification, i.e. formation of an acetate.

After a reaction period of 48 hours the process was terminated. The organic part representing the crude reaction product was separated from the aqueous part. The crude reaction product was washed twice with 100 ml. of warm water to remove the adhering sulfuric acid. It was estimated that the reaction product contained 10% of the acetate of 3-methyl-2-nonen-1-ol. A solution of 20 g. of sodium hydroxide in 200 ml. of water and 200 ml. of methanol was added to the reaction product and the solution was refluxed for 4 hours in order to saponify the ester. The methanol was removed by distillation under a slight vacuum through a 14" column packed with small glass rings. The remaining reaction product was washed successively with 500 ml. of water, twice with 100 ml. of sodium bicarbonate solution, and 200 ml. of water.

Fractional distillation through a 14" column packed with small glass rings at a 10 mm. vacuum gave the following results:

| Vapor-Temperature | Weight | R.I. 20° C. | |
|---|---|---|---|
| 57°-70° C. | 85 g. | 1.4593 | hydrocarbons |
| 71°-84° C. | 16 g. | 1.4516 | intermediate section mixture of hydrocarbons and starting alcohol |
| 85°-88° C. | 190 g. | 1.4438 | starting material (alcohol) |
| 90°-109° C. | 30 g. | 1.4582 | mixture of the |

-continued

| Vapor-Temperature | Weight | R.I. 20° C. | |
|---|---|---|---|
| 110°-111° C. | 149 g. | 1.4552 | starting material (alcohol) plus the rearranged alcohol (3-methyl-2-nonen-1-ol) (rearranged alcohol) |
| Residue: | 30 g. | | |
| | 500 g. | | |

EXAMPLE VIII

PREPARATION OF 3-METHYL-NONAN-1-OL

52 G. of 3-methyl-2-nonen-1-ol were hydrogenated for 4 hours in the presence of Raney nickel catalyst at an initial pressure of 50 pounds per square inch until the theoretical amount of hydrogen was consumed. The hydrogenated material was fractionated through a ½ foot Vigreux column. 48.6 G. distilled at 108° C. under 10 mm. pressure, representing the desired 3-methylnonan-1-ol. The product had a refractive index at 20° C. of 1.4384. There was a residue of 3.4 g.

EXAMPLE IX

PREPARATION OF 3-METHYL-2-NONEN-1-YL ACETATE

156 G. (1 mole) of 3-methyl-2-nonen-1-ol, 122 g. (1.2 moles) of acetic anhydride and 264 ml. of toluene were combined in a reaction flask and heated. The formed acetic acid-toluene azeotropic mixture consisting of 34 parts of acetic acid and 66 parts of toluene and boiling at 105° C. was removed by distillation through a 1½ ft. Vigreux column. After termination of the reaction, the reaction mass was washed with 100 ml. of aqueous sodium carbonate solution, 100 ml. of aqueous sodium bicarbonate solution, and finally twice with 100 ml. of water. The desired ester, 3-methyl-2-nonen-1-yl-acetate, having a b.p. of 119°-121° C. at 10 mm. and an R.I. at 20°:1.445, was recovered by fractional distillation.

EXAMPLE X

PREPARATION OF 3-METHYL-2-NONEN-YL-ISOBUTYRATE

156 G. (1 mole) of 3-methyl-2-nonen-1-ol, 158 g. (1.2 moles) of isobutyric anhydride and 1..20 g. of m-xylene were combined in a reaction flask and heated. The formed isobutyric acid-m-xylene azeotropic mixture consisting of 14 parts isobutyric acid and 86 parts m-xylene and boiling at 135.8° C. was removed by distillation through a 1½ ft. Vigreux column. It is advisable and advantageous to add another 400-500 ml. of m-xylene to the reaction mixture in the course of the reaction. After termination of the reaction, the reaction mass was washed with 100 ml. of aqueous sodium carbonate, 100 ml. of aqueous sodium bicarbonate solution and finally twice with 100 ml. of water. The desired ester, 3-methyl-2-nonen-1-yl-isobutyrate, having a b.p. of 121° C. at 5 mm., was recovered by fractional distillation. The refractive index of the product at 20° C. was 1.4399.

EXAMPLE XI

PREPARATION OF 3-METHYLNONAN-3-YL-SALICYLATE 40.0 G (0.25 mole) of 3-methylnonan-3-ol, 20. -g. of pyridine and 60 ml. of hexane are combined and cooled to 5° C. under agitation. To the resulting solution is added, under agitation over a period of 1 to 2 hours while maintaining the reaction temperature between 5°-15° C., a solution of 39 g. (0.25 mole) of 2-hydroxybenzoylchloride (salicylic-acid-chloride) dissolved in 60 ml. of hexane. The source of cooling is removed and the reaction mixture is agitated overnight, permitting the temperature of the reaction mixture to rise to room temperature (25°-30° C.). After completion of the reaction, the formed pyridine hydrochloride is removed by successive washings with 100 ml. of warm water. The solvent is removed by distillation and the desired ester is rectified by fractional distillation in a vacuum, preferably at 1 mm.

EXAMPLE XII

PREPARATION OF 3-METHYL-1-NONEN-3-YL-SALICYLATE

The procedure in Example XI is followed except that 39 g. of 3-methyl-1-nonen-3-ol instead of 40 g. of 3-methylnonan-3-ol are brought into the reaction.

EXAMPLE XIII

PREPARATION OF 3-METHYLNONAN-1-YL-SALICYLATE

The procedure in Example XI is followed except that 39 g. of 3-methyl-nonan-1-ol instead of 40 g. of 3-methylnonan-3-ol are brought into the reaction.

EXAMPLE XIV

PREPARATION OF 3-METHYL-2-NONEN-1-YL-SALICYLATE

The procedure in Example XI is followed except that 39 g. of 3-methyl-2-nonen-1-ol instead of 40 g. of 3-methylnonan-3-ol are brought into the reaction.

EXAMPLE XV

PREPARATION OF 3-METHYLNONAN-3-YL-PARA-TOLUIC ACID-ESTER 40.0 G. (0.25 mole) of 3-methylnonan-3-ol, 20 g. of pyridine and 60 ml. of hexane are combined and cooled to 5° C. under agitation. To the resulting solution is added, under agitation over a period of 1 to 2 hours while maintaining the reaction temperature between 5°-15° C. a solution of 39 g. (0.25 mole) of toluic acid chloride (para-methyl-benzoyl chloride) dissolved in 60 ml. of hexane. The source of cooling is removed and the reaction mixture is agitated overnight, permitting the temperature of the reaction mixture to rise to room temperature (25°-30° C.). After completion of the reaction, the formed pyridine hydrochloride is removed by successive washings with 100 ml. portions of warm water. The solvent is removed by distillation and the desired ester is rectified by fractional distillation in a vacuum, preferably at 1 mm.

EXAMPLE XVI

PREPARATION OF 3-METHYL-1-NONEN-3-PARA-TOLUIC ACID ESTER

The procedure in Example XV is followed except that 39 g. of 3-methyl-1-nonen-3-ol instead of 40 g. of 3-methylnonan-3-ol are brought into the reaction.

EXAMPLE XVII

PREPARATION OF 3-METHYLNONAN-1-YL-PARA-TOLUIC ACID ESTER

The procedure in Example XV is followed except that 39 g. of 3-methyl-1-nonanol instead of 40 g. of 3-methylnonan-3-ol are brought into the reaction.

EXAMPLE XVIII

PREPARATION OF 3-METHYL-2-NONEN-1-YL-PARA-TOLUIC ACID ESTER

The procedure in Example XV is followed except that 39 g. of 3-methyl-2-nonen-1-ol instead of 40 g. of 3-methylnonan-3-ol are brought into the reaction.

EXAMPLE XIX

PREPARATION OF 3-METHYLNONAN-3-YL-HEXAHYDROBENZOATE

36 G. (0.25 mole) of 3-methylnonan-3-ol, 20 g. of pyridine and 60 ml. of hexane are combined and cooled to 5° C. under agitation. To the resulting solution is added, under agitation over a period of 1 to 2 hours while maintaining the reaction temperature between 5°-15° C. a solution of 37 g. (0.25 mole) hexahydrobenzoyl-chloride dissolved in 60 ml. of hexane. The source of cooling is removed and the reaction mixture is agitated overnight, permitting the temperature of the reaction mixture to rise to room temperature (25°-30° C.). After completion of the reaction, the formed pyridine hydrochloride is removed by successive washings with 100 ml. portions of warm water. The solvent is removed by distillation and the desired ester is rectified by fractional distillation in a vacuum, preferably at 1 mm.

EXAMPLE XX

PREPARATION OF 3-METHYL-1-NONEN-3-YL-HEXAHYRDOBENZOATE

The procedure in Example XIX is followed except that 39 g. of 3-methyl-1-nonen-3-ol instead of 40 g. of 3-methylnonan-3-ol are brought into the reaction.

EXAMPLE XXI

PREPARATION OF 3-METHYLNONAN-1-YL-HEXAHYDROBENZOATE

The procedure in Example XIX is followed except that 39 g. of 3-methylnonan-1-ol instead of 40 g. of 3-methylnonan-3-ol are brought into the reaction.

EXAMPLE XXII

PREPARATION OF 3-METHYL-2-NONEN-1-YL-HEXAHYDROBENZOATE

The procedure in Example XIX is followed except that 39 g. of 3-methylnonan-1-ol instead of 40 g. of 3-methylnonan-3-ol are brought into the reaction.

EXAMPLE XXIII

COLONIA PERFUME COMPOSITION

A colonia perfume composition is prepared by mixing together the following:

| Parts: | Component: |
|---|---|
| 0.3 | civet artificial |
| 0.2 | resinoid benzoin siam |
| 0.2 | resinoid opoponax |
| 0.5 | ethyl vanillin |
| 0.8 | ambergris artificial F.B. |
| 1.0 | Fritzbro ylang synthetic |
| 1.0 | oil rosemary |
| 2.0 | musk ambrette |
| 2.0 | F.B. synthetic flower oil Dianthus |
| 3.0 | oil petitgrain bigarade |
| 17.5 | oil sweet orange |
| 16.5 | oil bergamot |
| 27.5 | oil lemon |
| 27.5 | 3-methylnonan-3-yl-acetate |
| 100. | |

EXAMPLE XXIV

FRUITY BOUQUET PERFUME COMPOSITION

Fruity bouquet compositions are produced by mixing together components in either of the following formulations:

| FRUITY BOUQUET #1. | |
|---|---|
| Parts: | Component: |
| 1.5 | 3-methylnonan-3-yl-formate |
| 2.5 | heliotropine |
| 5.0 | musk ketone |
| 6.5 | methyl ionone |
| 15.0 | F.B. synthetic lily of the valley |
| 19.5 | F.B. synthetic red rose |
| 45.0 | 3-methylnonan-3-ol |
| 5.0 | 3-methyl-1-nonen-3-yl-heptanoate |
| 100.0 | |

The 3-methyl-1-nonen-3-yl-heptanoate employed in any of the examples is produced in the same manner as 3-methyl-1-nonen-3-yl-isobutyrate is prepared in accordance with Example V, except that heptanoic acid anhydride is used instead of isobutyric acid anhydride.

| FRUITY BOUQUET #2. | |
|---|---|
| Parts: | Component: |
| 1.0 | 3-methylnonan-3-yl-formate |
| 1.0 | heliotropine |
| 1.0 | musk ketone |
| 1.0 | methyl ionone |
| 3.0 | F.B. synthetic lily of the valley |
| 3.0 | F.B. synthetic red rose |
| 90.0 | 3-methyl-1-nonen-3-yl-heptanoate |
| 100.0 | |

EXAMPLE XXV

GARDENIA PERFUME COMPOSITIONS

Gardenia perfume compositions are prepared by mixing together components in either of the following formulations:

| GARDENIA #1. | |
|---|---|
| Parts: | Component: |
| 2.0 | 3-methylnonan-3-yl-acetate |
| 0.2 | aldehyde C 10 |
| 0.3 | aldehyde C 11 |
| 1.5 | oil sandalwood E. I. |
| 1.5 | styrolyl acetate |

-continued

| GARDENIA #1. | |
|---|---|
| Parts: | Component: |
| 1.5 | coumarin |
| 1.5 | resinoid labdanum absolute |
| 2.5 | musk ketone |
| 4.0 | iso eugenol |
| 8.0 | F.B. synthetic violet parma type |
| 8.0 | oil bergamot |
| 12.5 | F.B. synthetic otto rose |
| 16.4 | F.B. synthetic lilac |
| 40.1 | 3-methyl-1-nonen-3-yl-isobutyrate |
| 100.0 | |

| GARDENIA #2. | |
|---|---|
| Parts: | Component: |
| 1.1 | 3-methyl-1-nonen-3-yl-acetate |
| 0.2 | aldehyde C 10 |
| 0.3 | aldehyde C 11 |
| 1.5 | oil sandalwood E. I. |
| 1.5 | styrolyl acetate |
| 1.5 | coumarin |
| 1.5 | resinoid labdanum absolute |
| 2.5 | musk ketone |
| 4.0 | iso eugenol |
| 8.0 | F.B. synthetic violet parma type |
| 8.0 | oil bergamot |
| 12.5 | F.B. synthetic otto rose |
| 16.4 | F.B. synthetic lilac |
| 41.0 | 3-methylnonan-3-yl-isobutyrate |
| 100.0 | |

EXAMPLE XXVI

JASMINE PERFUME COMPOSITIONS

Jasmine perfume compositions are prepared by mixing together components in accordance with the following formulations:

| JASMINE #1 | |
|---|---|
| Parts: | Component: |
| 1.5 | 3-methylnonan-3-yl-isobutyrate (or 3-methylnonan-3-yl-tiglate) |
| 1.5 | benzyl formate |
| 2.5 | linalyl acetate synthetic |
| 3.0 | benzyl salicylate |
| 3.5 | hexyl cinnamic aldehyde |
| 5.0 | rose de mai (Wardia replacement) |
| 5.0 | cinnamic alcohol |
| 6.0 | geraniol |
| 6.5 | F.B. synthetic flower oil linden blossom |
| 7.0 | tincture civet 4/128 D&O |
| 8.5 | Fritzbro jasmine provence |
| 20.0 | Fritzbro synthetic flavor oil ylang ylang |
| 30.0 | 3-methyl-1-nonen-3-yl acetate |
| 100.0 | |

| JASMINE #2 | |
|---|---|
| Parts: | Component: |
| 1.5 | 3-methylnonan-3-yl-isobutyrate |
| 1.5 | benzyl formate |
| 2.5 | linalyl acetate synthetic |
| 3.0 | benzyl salicylate |
| 3.5 | hexyl cinnamic aldehyde |
| 5.0 | rose de mai (Wardia replacement) |
| 5.0 | cinnamic alcohol |
| 6.0 | geraniol |
| 6.5 | F.B. synthetic flower oil linden blossom |
| 7.0 | tincture civet 4/128 (D&O) |

-continued

| JASMINE #2 | |
|---|---|
| Parts: | Component: |
| 8.5 | Fritzbro jasmine provence |
| 20.0 | Fritzbro synthetic flower oil ylang ylang |
| 25.0 | 3-methyl-1-nonen-3-yl-acetate |
| 5.0 | 3-methyl-1-nonen-3-yl-isovalerate (or 3-methyl-1-nonen-3-yl-acrylate) |
| 100.0 | |

The 3-methyl-1-nonen-3-yl-isovalerate employed in any of the examples is produced in the same manner as 3-methyl-1-nonen-3-yl-isobutyrate is prepared in accordance with Example V, except that isovaleric acid anhydride is used instead of isobutyric acid anhydride.

| JASMINE #3 | |
|---|---|
| Parts: | Component: |
| 10.0 | Fritzbro jasmine provence |
| 90.0 | 3-methyl-1-nonen-3-yl-isovalerate |
| 100.0 | |

EXAMPLE XXVII

LAVENDER NOTE COMPOSITIONS

Lavender note perfume compositions are prepared by mixing together components in accordance with the following formulations:

| LAVENDER NOTE #1 | |
|---|---|
| Parts: | Component: |
| 1.0 | oil patchouli |
| 2.0 | musk ketone |
| 2.0 | oil vetiver bourbon |
| 3.0 | musk ambrette |
| 4.0 | nerol C.F.B. |
| 5.0 | coumarin |
| 5.0 | oil lemon |
| 9.0 | heliotropine |
| 69.0 | 3-methylnonan-3-yl-acetate |
| 100.0 | |

| LAVENDER NOTE #2 | |
|---|---|
| Parts: | Component: |
| 1.0 | oil patchouli |
| 1.0 | musk ketone |
| 1.0 | oil vetiver bourbon |
| 1.0 | musk ambrette |
| 1.0 | nerol C.F.B. |
| 1.0 | coumarin |
| 1.0 | oil lemon |
| 3.0 | heliotropine |
| 90.0 | 3-methylnonan-3-yl-cyclopentane-carboxylate |
| 100.0 | |

The 3-methylnonan-3-yl-cyclopentanecarboxylate employed in any of the examples is produced in the same manner as 3-methylnonan-3-yl-isobutyrate is prepared in accordance with Example II, except that cyclopentanecarboxylic acid anhydride is used instead of isobutyric acid anhydride.

| LAVENDER NOTE #3 | |
|---|---|
| Parts: | Component: |
| 1.0 | oil patchouli |
| 2.0 | musk ketone |
| 2.0 | oil vetiver bourbon |
| 3.0 | musk ambrette |
| 4.0 | nerol C.F.B. |
| 5.0 | coumarin |
| 5.0 | oil lemon |
| 9.0 | heliotropine |
| 64.0 | 3-methylnonan-3-yl-acetate |
| 5.0 | 3-methylnonan-3-yl-cyclopentane-carboxylate (or 3-methylnonan-3-yl-crotonate) |
| 100.0 | |

EXAMPLE XXVIII

LILAC PERFUME COMPOSITIONS

Lilac perfume compositions are prepared by mixing together components in accordance with the following formulations:

| LILAC #1 | |
|---|---|
| Parts: | Component: |
| 1.0 | Wardia replacement |
| 2.5 | 10% sol. phenyl acetaldehyde in D.E.P. |
| 2.5 | benzyl acetate |
| 2.5 | hydroxy citronellal |
| 2.5 | amyl cinnamic aldehyde |
| 5.0 | lianyl acetate synthetic |
| 5.5 | jasolea base |
| 5.0 | musk ketone |
| 8.0 | heliotropine |
| 10.0 | F.B. synthetic ylang |
| 10.0 | cinnamic alcohol |
| 41.0 | 3-methyl-1-nonen-3-ol |
| 4.5 | durofix |
| 100.0 | |

| LILAC #2 | |
|---|---|
| Parts: | Component: |
| 10.0 | jasolea base |
| 90.0 | 3-methylnonan-3-yl-cyclohexanecarboxylate |
| 100.00 | |

| LILAC #3 | |
|---|---|
| Parts: | Component: |
| 1.0 | Wardia replacement |
| 2.5 | 10% sol. phenyl acetaldehyde in D.E.P. |
| 2.5 | benzyl acetate |
| 2.5 | hydroxycitronellal |
| 2.5 | amyl cinnamic aldehyde |
| 5.0 | linalyl acetate synthetic |
| 5.5 | jasolea base |
| 5.0 | musk ketone |
| 8.0 | heliotropine |
| 10.0 | F.B. synthetic ylang |
| 10.0 | cinnamic alcohol |
| 36.0 | 3-methyl-1-nonen-3-ol |
| 4.5 | durofix |
| 5.0 | 3-methylnonan-3-yl-cyclohexanecarboxylate |
| 100.0 | |

EXAMPLE XXIX

ROSE PERFUME COMPOSITION

A rose composition is prepared by mixing the following:

| Parts: | Component: |
|---|---|
| 1.5 | 3-methylnonan-3-yl-formate |
| 2.5 | heliotropine |
| 5.0 | musk ketone |
| 6.5 | methyl ionone |
| 15.0 | F.B. synthetic lily of the valley |
| 19.5 | F.B. synthetic red rose |
| 50.0 | 3-methylnonan-3-ol |
| 100.0 | |

EXAMPLE XXX

WOODY BOUQUET PERFUME COMPOSITIONS

Woody bouquet compositions are prepared by mixing together in accordance with the following formulation:

| WOODY BOUQUET #1 | |
|---|---|
| Parts: | Component: |
| 4.0 | oil geranium bourbon |
| 8.0 | 10% sol. methyl heptine carbonate in D.E.P. |
| 8.0 | alpha ionone |
| 12.0 | iso eugenol |
| 12.0 | oil bois de rose |
| 12.0 | phenyl ethyl alcohol |
| 12.0 | cinnamic alcohol |
| 32.0 | methyl ionone |
| 900.0 | 3-methyl-1-nonen-3-yl-cinnamate |
| 1000.0 | |

The 3-methyl-1-nonen-3-yl-cinnamate employed in any of the examples is produced in the same manner as 3-methyl-1-nonen-3-yl-isobutyrate is prepared in accordance with Example V, except that cinnamic acid anhydride is used instead of isobutyric acid anhydride.

| WOODY BOUQUET #2 | |
|---|---|
| Parts: | Component: |
| 5.0 | oil geranium bourbon |
| 8.0 | 10% sol. methyl heptine carbonate in diethyl phthalate |
| 8.0 | alpha ionone |
| 8.0 | oil cedarwood |
| 12.0 | oil bois de rose |
| 18.0 | phenyl ethyl alcohol |
| 18.0 | cedryl acetate |
| 23.0 | 3-methylnonan-3-yl-salicylate |
| 100.0 | |

| WOODY BOUQUET #3 | |
|---|---|
| Parts: | Component: |
| 2.0 | oil balsam peru |
| 2.0 | iso eugenol |
| 2.0 | methyl ionone |
| 2.0 | coumarin |
| 10.0 | oil cedarwood |
| 10.0 | cedryl acetate |
| 10.0 | oil vetiver haiti |
| 10.0 | geranyl acetate |
| 52.0 | 3-methylnonan-3-yl-hexahydrobenzoate |

-continued

| Parts: | Component: |
| --- | --- |
| | WOODY BOUQUET #3 |
| 100.0 | |

| Parts: | Component: |
| --- | --- |
| | WOODY BOUQUET #4 |
| 1.0 | oil eucalyptus 80/90% eucalyptol |
| 1.0 | oil sandalwood |
| 1.0 | geranyl acetate |
| 1.0 | phenyl ethyl acetate |
| 2.0 | oil cedarwood |
| 14.0 | 3-methylnonan-3-yl-hexahydrobenzoate |
| 25.0 | linalool synthetic |
| 25.0 | linalyl acetate synthetic |
| 30.0 | 3-methyl-1-nonen-3-yl-para-toluate |
| 100.0 | |

| Parts: | Component: |
| --- | --- |
| | WOODY BOUQUET #5 |
| 1.0 | eucalyptol |
| 1.0 | oil caraway |
| 2.0 | myrcene |
| 2.0 | methyl heptenone |
| 2.0 | nerol |
| 5.0 | geraniol |
| 5.0 | 3-methyl-2-nonen-1-yl-hexahydrobenzoate |
| 7.0 | 3-methylnonen-3-yl-salicylate |
| 12.0 | linalyl acetate synthetic |
| 20.0 | 3-methyl-2-nonen-1-yl-para-toluate |
| 20.0 | alpha terpineol |
| 23.0 | linalool synthetic |
| 100.0 | |

The perfume compositions containing 3-methylnonan-1-ol, 3-methyl-2-nonen-1-ol and monocarboxylic acid esters of these alcohols may be produced in the same manner as the compositions described in Examples XI through XVIII were prepared except that whenever 3-methylnonan-3-ol is used the same quantity of 3-methylnonan-1-ol is substituted therefor; whenever 3-methyl-1-nonen-3-ol is used, the same quantity of 3-methyl-2-nonen-1-ol is employed, and finally whenever a monocarboxylic ester of the 3-ol alcohols is specified, the corresponding monocarboxylic acid ester of the respective corresponding saturated or unsaturated 1-ol alcohols is employed. Such composition with the 1-ol alcohols and their corresponding monocarboxylic acid esters are satisfactory perfume compositions.

In the perfume compositions defined in the appended claims, one or a plurality of recited members may be included in such compositions, the defined quantitative values being the total of said members present.

What is claimed is:

1. A perfume composition comprising at least 9% by weight of a perfume component and at least 1% by weight of a member which enhances the odoriferous properties of said perfume component selected from the group consisting of 3-methylnonan-3-ol, 3-methyl-1-nonen-3-ol, 3-methylnonan-1-ol, 3-methyl-2-nonen-1-ol, esters produced by reaction of any of said specified alcohols with a monocarboxylic acid selected from the group consisting of saturated 1 to 7 carbon atoms aliphatic monocarboxylic acids, unsaturated 3 to 7 carbon atoms aliphatic monocarboxylic acids having one double bond, cyclopentane carboxylic acid, cyclohexane carboxylic acid, salicylic, cinnamic, hexahydrobenzoic and p-toluic acid.

2. A perfume composition of claim 1 in which the specified alcohol or specified ester comprises 1 to 91% by weight of the perfume composition.

3. A perfume composition of claim 1 in which the specified alcohol or specified ester comprises 2 to 88% by weight of the perfume composition.

4. A perfume composition of claim 1 in which the specified alcohol or specified ester comprises 5 to 85% by weight of the perfume composition.

5. A perfume composition of claim 1 in which said member is 3-methylnonan-3-ol.

6. A perfume composition of claim 1 in which said member is 3-methyl-1-nonen-3-ol.

7. A perfume composition of claim 1 in which said member is 3-methylnonan-1-ol.

8. A perfume composition of claim 1 in which said member is 3-methyl-2-nonen-1-ol.

9. A perfume composition of claim 1 in which said member is a monocarboxylic acid ester of 3-methylnonan-3-ol.

10. A perfume composition of claim 1 in which said member is a monocarboxylic acid ester of 3-methyl-1-nonen-3-ol.

11. A perfume composition of claim 1 in which said member is a monocarboxylic acid ester of 3-methylnonan-1-ol.

12. A perfume composition of claim 1 in which said member is a monocarboxylic acid ester of 3-methyl-2-nonen-1-ol.

13. A perfume composition of claim 1 in which said member is an ester produced by reaction of any of the specified alcohols with a saturated 1 to 7 carbon atoms aliphatic monocarboxylic acid.

14. A perfume composition of claim 1 in which said member is an acetate.

15. A perfume composition of claim 1 in which said member is an ester produced by reaction of any of the specified alcohols with an unsaturated 3 to 7 carbon atoms aliphatic monocarboxylic acid having one double bond.

* * * * *